(12) United States Patent
Bertram et al.

(10) Patent No.: US 9,612,657 B2
(45) Date of Patent: Apr. 4, 2017

(54) 3D-VOLUME VIEWING BY CONTROLLING SIGHT DEPTH

(71) Applicant: Brainlab AG, Feldkirchen (DE)

(72) Inventors: Pascal Bertram, München (DE); Dirk Staneker, München (DE)

(73) Assignee: Brainlab AG, Feldkirchen (DE)

( * ) Notice: Subject to any disclaimer, the term of this patent is extended or adjusted under 35 U.S.C. 154(b) by 11 days.

(21) Appl. No.: 14/775,480

(22) PCT Filed: Mar. 14, 2013

(86) PCT No.: PCT/EP2013/055242
§ 371 (c)(1),
(2) Date: Sep. 11, 2015

(87) PCT Pub. No.: WO2014/139574
PCT Pub. Date: Sep. 18, 2014

(65) Prior Publication Data
US 2016/0026243 A1    Jan. 28, 2016

(51) Int. Cl.
*G09G 5/00* (2006.01)
*G06F 3/01* (2006.01)
(Continued)

(52) U.S. Cl.
CPC .......... *G06F 3/013* (2013.01); *G06F 3/04815* (2013.01); *G06T 15/08* (2013.01);
(Continued)

(58) Field of Classification Search
CPC ........ G06F 3/013; G06F 3/015; G06F 3/0481; G06F 3/04815
See application file for complete search history.

(56) References Cited

U.S. PATENT DOCUMENTS 5,526,812 A * 6/1996 Dumoulin ............... G06F 3/013
345/7
8,457,352 B2    6/2013 Hennessey et al.
(Continued)

OTHER PUBLICATIONS

Andrew T. Duchowski, "Binocular Eye Tracking in VR for Visual Inspection Training", Clemson University, VRST'01, Nov. 15-17, 2001, Banff, Alberta, Canada, pp. 1-8.
(Continued)

*Primary Examiner* — Vijay Shankar
(74) *Attorney, Agent, or Firm* — Middleton Reutlinger

(57) ABSTRACT

A medical image data processing method for determining a set of medical image data to be displayed, the data processing method being constituted to be executed by a computer and comprising the following steps: a) acquiring medical image data comprising three-dimensional medical image information describing an anatomical structure, and displaying the medical image information; b) acquiring navigation display feature data comprising navigation display feature information describing at least one graphical navigation feature; c) displaying the navigation display information simultaneously with the medical image information; d) acquiring viewing direction data comprising viewing direction information describing a spatial relationship of a viewing direction of a user relative to the position of the at least one graphical navigation feature; e) determining, based on the viewing direction data, image information subset data comprising image data subset information describing a subset of the medical image information to be selected for display.

13 Claims, 4 Drawing Sheets

(51) Int. Cl.
G06F 3/0481 (2013.01)
H04N 13/00 (2006.01)
H04N 13/04 (2006.01)
G06T 15/08 (2011.01)

(52) U.S. Cl.
CPC ......... *H04N 13/004* (2013.01); *H04N 13/044* (2013.01); *H04N 13/0484* (2013.01)

(56) References Cited

U.S. PATENT DOCUMENTS

| | | | | |
|---|---|---|---|---|
| 2002/0075286 A1* | 6/2002 | Yonezawa | ............ | G02B 27/017 345/679 |
| 2002/0183607 A1* | 12/2002 | Bauch | .................... | G06T 19/00 600/407 |
| 2013/0187955 A1* | 7/2013 | Mezger | ................ | G06F 19/321 345/649 |

OTHER PUBLICATIONS

Hunter Murphy, "Gaze-Contingent Level of Detail Rendering", Clemson University, Department of Computer Science, Eurographics 2001, Clemson, SC, pp. 1-10.

* cited by examiner

3D-VOLUME VIEWING BY CONTROLLING SIGHT DEPTH

The present invention relates to a medical image data processing method for determining a set of medical image data to be displayed in accordance with claim 1. The invention further relates to a program that, when running on a computer or when loaded onto a computer, causes that computer to perform the steps of the method, a signal wave carrying information which represents that program and a computer running that program. Furthermore, the invention relates to a viewing system for viewing medical image information which comprises in particular the aforementioned computer.

In particular when assessing the characteristics of an anatomical region for planning a medical procedure (such as for example radiotherapy), it may be necessary for a user such as a physician or a medical technician to acquire a visual impression of the relevant anatomical structure. To this end, three-dimensional medical image data is commonly displayed for example on a monitor. The three-dimensional image data may be generated by planar reconstructions or volumetric projections of individual images of the anatomical structure. However, a method using planar reconstructions is inherently limited to displaying sliced image data. With using volumetric projections, a need arises for rendering parts of the displayed volume of image data transparent so that an image of the desired anatomical structure becomes visible to the user. In order to create such a transparent volume, a-priori knowledge of the image data describing the desired anatomical structure is necessary. Without such knowledge, no decision would be possible on which subset of the image data should be rendered transparent. This in turn results in difficulties in changing the display to a different desired anatomical structure. This non-linear change of transparency limits the display of unaltered raw data.

In this regard, the present invention provides the advantage of efficiently determining, during display of a specific desired anatomical structure, a different desired anatomical structure to be displayed and to thus enable a user to quickly switch between images of anatomical structures described by volumetric medical image information.

A problem to be solved by the present invention therefore is to provide a method of displaying medical image data which allows to quickly switch between displays of different parts of the medical image data while preserving the values of the raw data during display.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

EXEMPLARY SHORT DESCRIPTION OF THE PRESENT INVENTION

In the following, a concise description of the present invention is offered which is to be considered merely as an example and not as a limitation of the invention to the features described in the following.

The present invention provides in particular for a data processing method for processing medical image data in which, first of all, three-dimensional medical image information describing an anatomical structure is acquired and displayed. Preferably as an overlay to the medical image information, at least one graphical navigation feature is displayed. Furthermore, information describing a viewing direction which is represented in particular by a point of gaze of a user is acquired and, depending on the position of the point of gaze relative to the graphical navigation feature, the user is allowed to scroll through different images representing each a part of the anatomical structure described by the medical image information.

GENERAL DESCRIPTION OF THE INVENTION

In this section, a general description of the features and embodiments of the present invention is offered. The features described in the following constitute preferred and particular features of the invention.

At the end of this section, definitions are disclosed which define a meaning of specific terminology used in the present disclosure. These definitions also form part of the present disclosure.

The present invention as a first invention is directed to a data processing method, more particularly a medical image data processing method, for determining a set of medical image data to be displayed. The data processing method according to the first invention is preferably constituted to be executed by a computer and preferably comprises the following steps:

Preferably, medical image data is acquired which comprises medical image information. The medical image information is preferably three-dimensional and preferably describes an anatomical structure. In particular, the medical image information describes an image of the anatomical structure in three dimensions, and may therefore also be said to be volume image information or volumetric image information. Preferably, the medical image information is also displayed in particular on a display unit. More particularly, the computer executing the inventive method controls the display unit to display the medical image information. The display unit is in particular a standard monitor for displaying graphical information output from a computer such as a TFT monitor or a plasma monitor. Alternatively, the display unit may comprise a projector (beamer) and screen onto which the projector projects the medical image information. The display unit preferably is configured to display a different set (i.e. different disjunct sets) of medical image information to the left and the right eye. For example, the display unit is embodied by a head-up display comprising display goggles (e.g. in a head-mounted display) with a different projection plane (screen) for each eye of the user. Advantageously, the display unit is a monitor having a preferably known and advantageously fixed spatial relationship (in particular position and/or orientation) relative to an eye-tracking unit.

The medical image information describes in particular any kind of anatomical structure, i.e. any part of a human or animal body. Preferably, the anatomical structure contains solid tissue, in particular at least one of soft tissue and bony tissue. Optionally, the anatomical may contain body fluids, for example at least one of blood and liquor (cerebrospinal fluid). For example, the anatomical structure comprises at least one of soft tissue (for example in case the anatomical structure is at least part of a brain) or a bony tissue (for example in case the anatomical structure is part of a bony structure, for example a joint between bones such as a knee).

Preferably, navigation display feature data is acquired which comprises navigation display feature information. The navigation display feature information describes in particular at least one graphical navigation feature. More particularly, the display feature information describes a plurality of (for example exactly two) graphical navigation features. The graphical navigation feature is in particular a graphical feature, i.e. graphical information, which is constituted to be output by a computer executing the disclosed method. Advantageously, the graphical navigation feature is designed such that a user can visually determine it as not representing part of the anatomical structure. Preferably, the navigation display information is displayed simultaneously with the medical image information, advantageously by the same display unit. Simultaneously displaying the navigation display information and the medical image information means in particular that they are displayed at the same time. For example, the graphical navigation feature may take the form of a three-dimensional sphere or a two-dimensional spot or be defined as the tip of an arrow pointing in a specific direction. The graphical navigation feature is preferably displayed as an overlay on the medical image information.

Preferably, viewing direction data is acquired which comprises viewing direction information. The viewing direction information describes in particular a special relationship (i.e. at least one of a position and an orientation) of a viewing direction of a user relative to the position of the at least one graphical navigation feature. Preferably, the viewing direction data is acquired based on tracking the eyes of the user with a tracking unit such as for example at least one camera and advantageously exactly two cameras. Preferably, the viewing direction information comprises point of gaze information about the position of a point of gaze of a user viewing the medical image information. The position of the point of gaze is determined advantageously by applying the method described by Duchowski et al., Binocular Eye Tracking in VR for Visual Inspection Training, VRST '01 Nov. 15-17, 2011, Banff, Alberta, Canada. In particular, a gaze vector is determined by tracking the pupils of the user's eyes and determining an intersection of the viewing direction of the user's eyes defined by the pupil position with image planes (display planes). The image planes resemble in particular the display unit by which the medical image information is displayed. In particular, the position of a display plane is defined as the position of a screen on which the medical image information and the navigation display information is displayed. The position of the pupils is tracked advantageously by cameras which advantageously have a known and preferably fixed position relative to the position of the display planes (and therefore to the position of the display unit). If the display is not head-mounted the position of the head advantageously is known.

The positions described by the viewing direction information and the navigation display feature information are preferably defined in or transformed into a reference system used to display the medical image information. As described above, the medical image information preferably is defined in three dimensions so as to describe an anatomical structure which itself is three-dimensional. In order to give a user a proper visual impression of the image wise appearance of the anatomical structure, the medical image information is therefore defined in a preferably three-dimensional reference system (in particular, a coordinate system such as a Cartesian or a spherical coordinate system) such that the spatial relationship of image features described by the medical image information relative to one another resembles, in particular is similar or equal, to the special relationship of the corresponding real features of the anatomical structure described by the medical image information.

Preferably, image information subset data is determined based on the viewing direction data. Further preferably, the image information subset data is determined based on also the medical image information. The image information subset data comprises in particular image data subset information which describes a subset of the medical image information to be selected for display. The subset of the medical image information (within the framework of this disclosure also simply termed "subset") preferably describes a continuous, in particular coherent, volume of which represents the whole or at least part of the anatomical structure described by the medical image information. The subset describes in particular a sub-volume of the corresponding part of the anatomical structure. The subset is then advantageously selected for display and preferably also displayed on the display unit. This feature supports the user's ability to control, based on his viewing direction relative to the position of the display of the graphical navigation feature on the display unit, which part of the anatomical structure shall be displayed in an image-wise fashion, in particular as an image.

Preferably, the position of the at least one graphical navigation feature rests relative to the positions of the image features described by the subset. This means in particular that, when the subset is determined and displayed, the position of the at least one graphical navigation feature as it is displayed on the display unit changes in accordance with the positions in the reference system which are assigned to the medical image information contained in the subset. For example, when moving through the medical image information and thereby moving between subsets, the user will thus get an impression of a moving of at least one graphical navigation feature. Alternatively, the position of the at least one graphical navigation feature rests in a reference system in which the positions of the medical image information is defined. This means in particular that the position of the at least one graphical navigation feature on the display unit remains constant irrespective of the positions in the reference system assigned to the medical image information in the subset. This provides the advantage that the user does not need to adapt his viewing direction to an ever-changing position of the at least one graphical navigation feature on the display device when moving through the image representation of the anatomical structure.

Preferably, the viewing direction information describes the position and orientation of the user's head in a reference system in which the positions of the medical image information is described. Information about this position and orientation may be gathered for example by an optical or electromagnetic or force-based or other tracking system with or without markers fixated on the user. In particular in this case it is advantageous to use a combined tracking unit and display unit which may be embodied by for example a head-mounted display (HMD). In particular in case the viewing direction information describes the position and orientation of the user's head, the image information subset data (in particular the image information subset information) is determined based on the information about the position and orientation of the user's head. For example, a perspective in which the medical image information contained in the subset is displayed as determined (in particular also displayed) in accordance with the information about the orientation.

Preferably, the medical image information, in particular each unit of the medical image information, is assigned a visibility value describing the opacity and/or transparency of the image information described by that unit. The visibility value is preferably designated as $\alpha$, and may vary in a range between $\alpha=0$ (designating complete transparency) and $\alpha=1$ (designating complete opacity). Values of a lying in the interval $0<\alpha<1$ denote partial transparency (or partial opacity, respectively) and thus, when serving as a basis for the displayed image information, give the user an impression of a kind of hazy picture in which he is able to view an image of at least traces of parts of the anatomical structure lying, from the user's perspective, behind those parts described by the medical image information in the subset. In particular, those parts of the anatomical structure lying, from the user's perspective, in front of the anatomical structure described by the medical image information in the subset are assigned a visibility value designating complete transparency. Those parts which are rendered transparent (in particular the positions of the medical image information representing them) are in particular traversed by the user's viewing direction and lie in between the position of the user's eyes and his point of gaze. Further preferably, the medical image information in the subset behind the subset described above, from the users's perspective, is assigned a visibility value designating complete opacity. In consequence, the user is able to view only medical image information contained in the subset, i.e. only this medical image information is visible for him or her.

According to a preferable embodiment, the image information contained in the subset of the medical image information is assigned a visibility value lying in between a value describing complete opacity and a value describing complete transparency, but is not assigned a visibility value describing complete opacity or complete transparency. In particular, the medical image information in the subset is assigned a visibility value fulfilling the condition of 0<visibility value<1 where 0 describes complete transparency and 1 describes complete opacity. An advantage of such a preferable embodiment is that the user is presented a semi-transparent image of a specific part of the anatomical structure described by the medical image information contained in the subset. This allows the user to visually determine other parts of the anatomical structure which, from his perspective, lie behind the part of the anatomical structure described by the medical image information in the subset. Thereby, the user is offered visual information which helps him to decide whether he shall navigate deeper into the image representation of the anatomical structure, i.e. further along his a line of sight away from his own position and into the virtual representation, i.e. image representation, of the anatomical structure. The user may therefore move through the medical image information in a three-dimensional manner, in particular control his depth of sight into the (volume of) medical image information.

In particular in the case of the medical image information in the subset being assigned a visibility value which describes complete opacity, the subset of the medical image information represents a visible image of a first part of the anatomical structure which lies in between a different, second part of the anatomical structure which is displayed in a transparent manner and a further different, third part of the anatomical structure which is occluded in the display, i.e. is not visible (invisible). Preferably, the second part lies further towards the position of the user compared to the position of the first part. In analogy, the position of the third part preferably lies further away from the position of the user than the position of the second part. These statements regarding positions of the first, second and third part and of the user are based on the assumption that the positions of both the first, second and third parts and of the user are defined in or at least transformed into a common reference system. In this preferable embodiment, the medical image information representing the second part describes an anatomical structure which lies in between the first part being closer to the position of the user and the third part being further away from the position of the user than the second part.

Preferably, the size of the second part of the anatomical structure, in particular the number of image units (such as pixels and/or voxels) in the medical image information representing the second part, is determined, in particular increased or decreased, based on the spatial relationship between the position of the at least one graphical navigation feature and the viewing direction of the user. More particularly, it is determined based on the spatial relationship between the position of the at least one graphical navigation feature and the position of the point of gaze of the user. For example, the volume and/or partial volume of the anatomical structure constituting the second part (and therefore to be rendered transparent in the image-wise representation of the anatomical structure according to the disclosed method) is increased when the viewing direction points towards a graphical navigation feature which indicates to move the position of the first part further away from the position of the user (in a common reference system) and/or if the position of the point of gaze is coincident with the position of the graphical navigation feature or lies within a predetermined position interval around the position of the graphical navigation feature. In analogy, the volume of the medical image information representing the second part may be decreased if the viewing direction points towards a graphical navigation feature indicating to move the position of the first part closer to the user's position (with a corresponding consequence of the point of gaze being coincident or lying within a predetermined interval of the position of such a graphical navigation feature).

According to a specific embodiment of the invention, the graphical navigation feature is not displayed in a manner which is visually discernible from the medical image information. Rather, the graphical navigation feature may be implemented as a position defined within the reference system used for displaying the medical image information. Such positions may be determined based on the position of the point of gaze of the user. For example, a point of interest having the respective position may be defined to lie at (i.e. to coincide with) the position of the point of gaze. A volume of image information (image volume) around the point of interest is then defined according to preferably predetermined dimensions of such an image volume, the image volume then being at least part of or identical with the image information contained in the subset. The image volume may also be defined in two dimensions, i.e. represent a slice of image information having a depth of in particular one image unit (i.e. one pixel and/or or one voxel) and extending in a plane which is preferably parallel to the position of the display unit in the common reference system in which the positions of medical image information and the user are processed, in particular defined. However, the planar extension of the image volume which is rendered visible to the user may also run in a direction which is not parallel, in particular runs at an angle between more than 0 degrees and less than 90 degrees relative to the image plane of the display unit. Such a feature may be in particular implemented if the viewing direction information also contains information on the orientation of the user's head.

Also disclosed herein is a second invention which is directed to a medical image data processing method for determining a set of medical image data processing method for determining a set of medical image data to be displayed, the data processing set being contributed to be executed by a computer and comprising the following steps:
a) acquiring medical image data comprising three-dimensional medical image information describing an anatomical structure;
b) acquiring visibility value data comprising visibility value information describing a visibility value for each part, in particular unit, of the medical image information;
c) selecting at least a subset of the medical image information for being displayed based on the visibility value data, in particular based on the visibility value information;
d) preferably, displaying the selected medical image information.

The visibility value corresponds in particular to the visibility value described in the context of the first invention. Therefore, the visibility value describes in particular a transparency or opacity, respectively, of in particular each image unit (for example, a pixel or voxel). For example, a subset of the medical image information such as a first (in particular coherent) volume (in particular block) of image units is assigned a visibility value which indicates complete transparency and a second, different, (in particular coherent) volume of image units which is advantageously contiguous and/or adjacent to the first volume is assigned a visibility volume representing at least partial opacity (i.e. not complete transparency, preferably complete opacity). The first volume preferably lies, from a user's perspective, between the position of the user and the positions of each image unit in the second volume. The second volume may be understood to comprise in particular only one layer of image units (i.e. a depth of one image unit) which is contiguous to the first volume. The second invention therefore has the effect that the user sees only the medical image information which is represented by in particular the first layer of image units of the second volume which is contiguous to the first volume. In particular, the user cannot view the medical image information represented by the image units of the first volume since they are rendered transparent.

The second invention may of course as far as technically feasible be combined with the features of the first invention. The definitions and explanations of terminology used for describing the first invention are also valid for the corresponding terminology used in the context of the second invention.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The invention also relates to a viewing system for viewing medical image information which comprises the aforementioned computer which in particular runs a program comprising code means for execution of the above-described method. The viewing system further preferably comprises the aforementioned computer which in particular runs a program comprising code means for execution of the above-described method. The viewing system further preferably comprises the above-described display unit for displaying the medical image information and the navigation display feature information as well as the above-described tracking unit for tracking the eyes (in particular the positions of the eyes, more particularly the positions of the pupils) of the user and preferably also for tracking the orientation of the user's head.

DEFINITIONS

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

In the field of medicine, imaging methods are used to generate image data (for example, two-dimensional or three-dimensional image data) of anatomical structures (such as soft tissues, bones, organs, etc.) of the human body. Such image data is also termed "medical image data" in the framework of this disclosure. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body.

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information". Wherever in this disclosure data processing is carried out on "XY data", it shall be understood that this processing is also carried out on the respective "XY information".

DESCRIPTION OF THE FIGURES

In the following, a preferred embodiment of the invention, which is to be understood as non-limiting to the scope of the invention but rather as a mere example, is disclosed with reference to the figures, wherein.

Figure 1A:
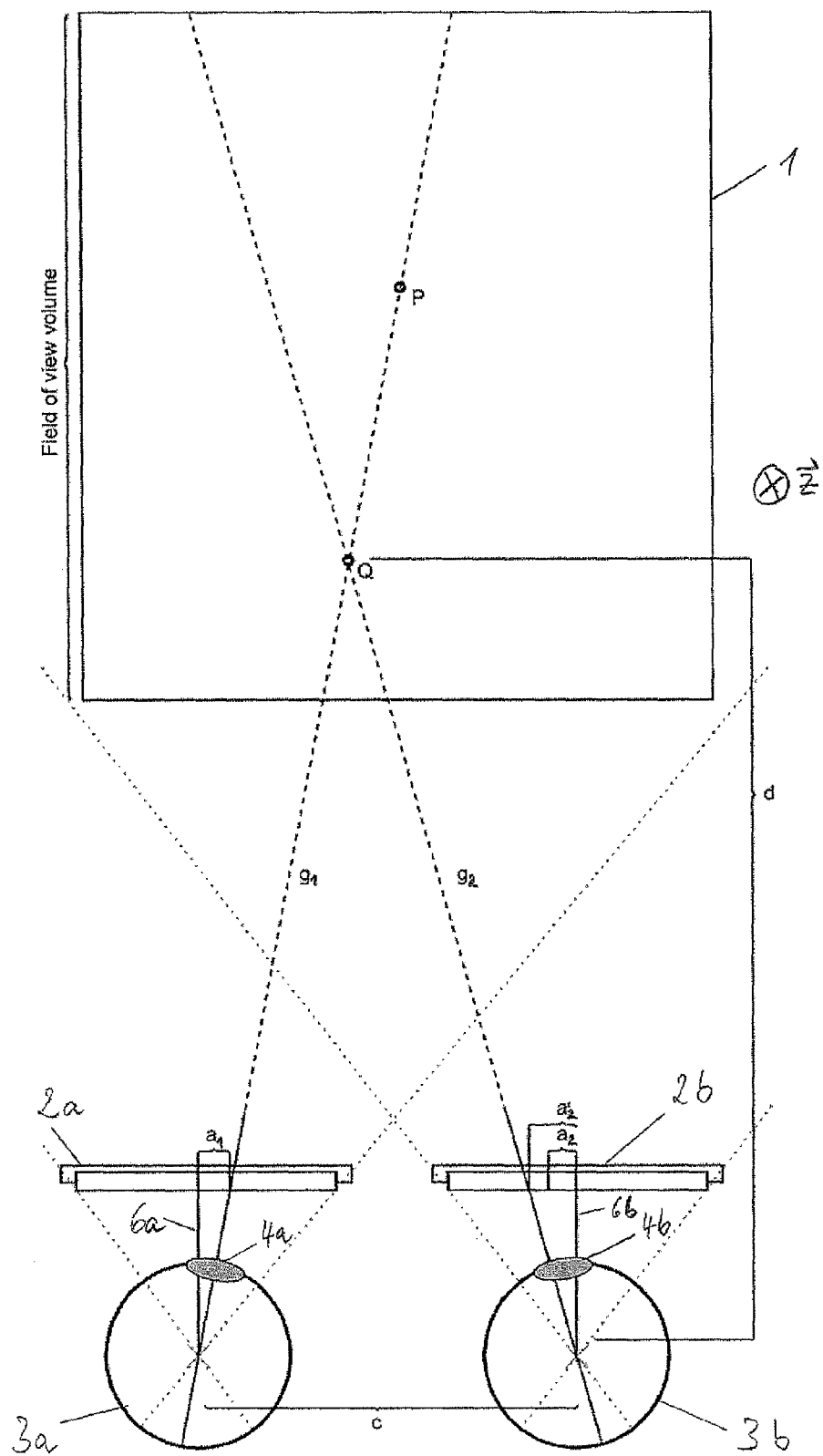
FIG. 1a shows the geometry for determining a first point of gaze.

According to FIG. 1a, a field of view volume 1 representing the medical image data is displayed on screens 2a, 2b embodying display units. A user views the medical image information contained in (in particular embodied by) the field of view volume 1 on the screens 2a, 2b with his eyes 3a, 3b having pupils 4a, 4b. In their neutral position, the eyes have a (central) neutral line of view 6a, 6b which runs perpendicular to the screens 2a, 2b. The centre points of the eyes 3a, 3b are spaced by a distance c. The user's current line of sight is denoted by $g_1$ for the left eye 3a and $g_2$ for the right eye 3b. In the depiction of FIG. 1a, the user is gazing at a point Q which has a (perpendicular) distance d from a plane running vertical to the drawing plane and to the centre points of both eyes 3a, 3b. The distance d is defined in a common reference system in which the positions of structures (image features) described by the field of view volume 1 and the positions of the eyes 3a, 3b are defined. The common reference system preferably is a rectangular coordinate system having three axes (x-, y- and z-axis) which are perpendicular to one another. In particular, the rectangular coordinate system is a three-dimensional Cartesian coordinate system. In particular, the coordinates of points Q and P are also defined in this reference system. The user thus gets a visual impression of for example the anatomical structure at the point of gaze Q having a spatial relationship (in particular, a distance and/or a position) relative to his eyes 3a, 3b which corresponds to the spatial relationship of Q and the eyes 3a, 3b in the aforementioned reference system. The position of the point of gaze Q is determined in particular on the basis of information about the position of an intersection of the line of view $g_1$, $g_2$ with the respective screen 2a, 2b. In the case of the left eye 3a, the line of view $g_1$ intersects the screen 2a at distance $a_1$ away from the intersection with the neutral line of view 6a with the screen 2a. In the case of the right eye 3b, the current line of view $g_2$ intersects the screen 2b at a distance $a_2'$ away from an intersection of the right-eye neutral line of view 6b with the screen 2b. Since $a_2'$ is greater than $a_2$, it determined that Q lies to the left of a plane (also termed "central plane" lying in the middle between the neutral lines of view 6a, 6b and perpendicular to the drawing plane. It is noted that, without having a second current line of sights $g_2$, the user would not be able to discern between image features displayed at the position of Q and image features displayed at the position of P. If, for example, the user had only a left eye 3a, he would be able to see only the image features displayed at Q since they are displayed, from the perspective of the user's eyes 3a, 3b in front of the image features at P along the left-eye current line of sight $g_1$. It is to be noted that the medical image information in the field of view volume 1 is three-dimensional and also comprises a third positional coordinate along a z-axis which runs perpendicular to the drawing plane.

Figure 1B:
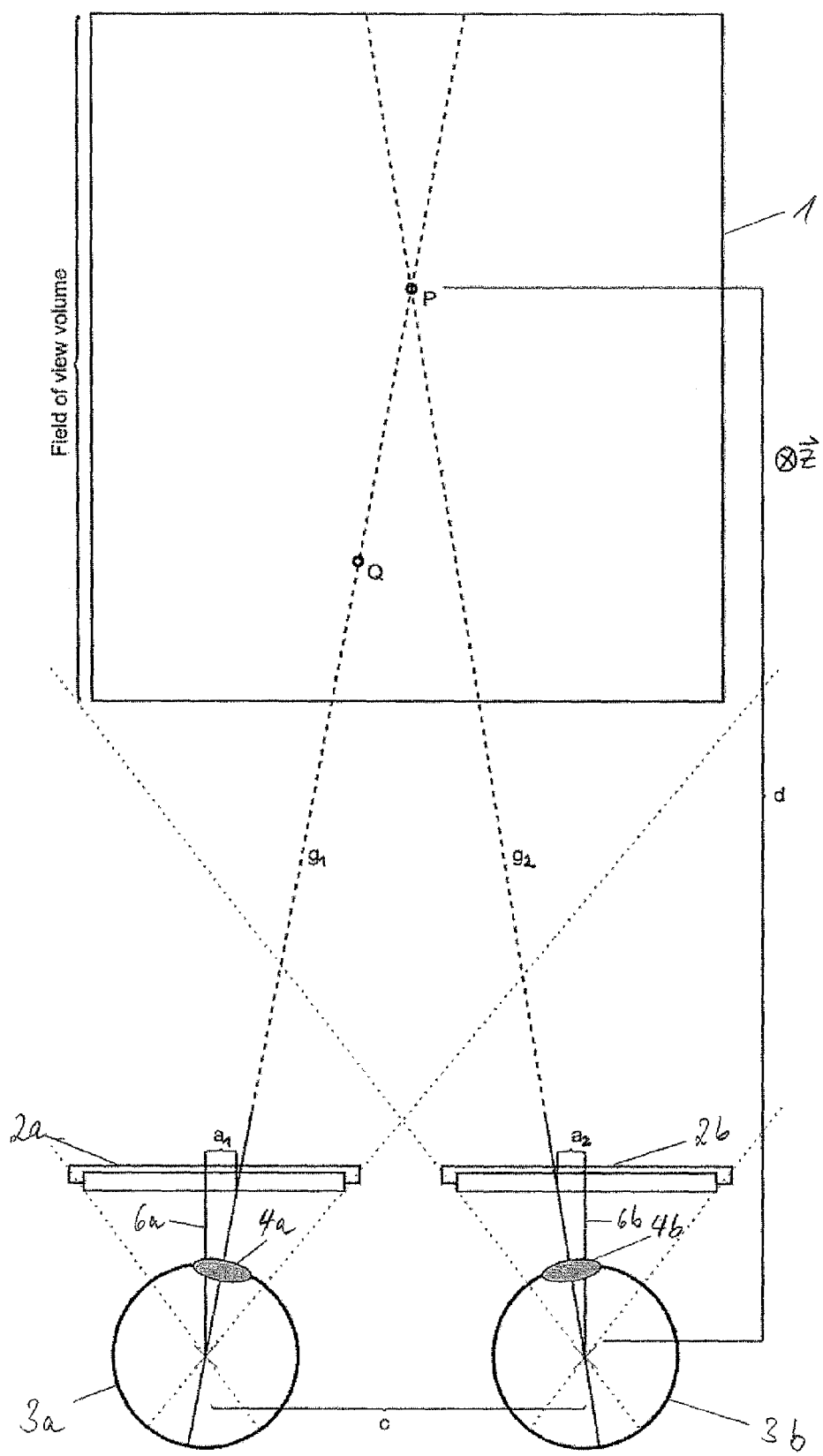
FIG. 1b shows the geometry for determining a second point of gaze which lies deeper in the field of view volume than the first point of gaze.

FIG. 1b shows the situation with a point of gaze located at the position of P, wherein $a_1 = a_2$. In this case, P lies in the central. However, from the point of view of the left eye 3a, Q lies in front of P along the left-eye current line of sight $g_1$. Therefore, the left eye 3a will receive visual information about the image features displayed at the position of Q, and the right eye 3b will receive visual information about the image features displayed at the position of P. Therefore, the user gets a three-dimensional visual impression and thus is able to perform spatial vision along in particular the coordinate axis in the drawing plane which runs parallel to the neutral lines of view 6a, 6b (which in turn advantageously lie in the drawing plane). In particular, the y- and x-axis of the common reference system lie in the drawing plane and at least of them is parallel to the neutral lines of view 6a, 6b.

The position of the point of gaze (which in the case of FIG. 1a is the point Q and in the case of FIG. 1b is the point P) is determined based on the triangular geometry described by c, d and $g_1$, $g_2$. The intersection of $g_1$ and $g_2$ is determined in particular based on information about the intersection of $g_1$ and the surface of the screen 2a and $g_2$ and the surface of screen 2b and/or on information about the magnitude of $a_1$ and $a_2$.

Figure 2A:
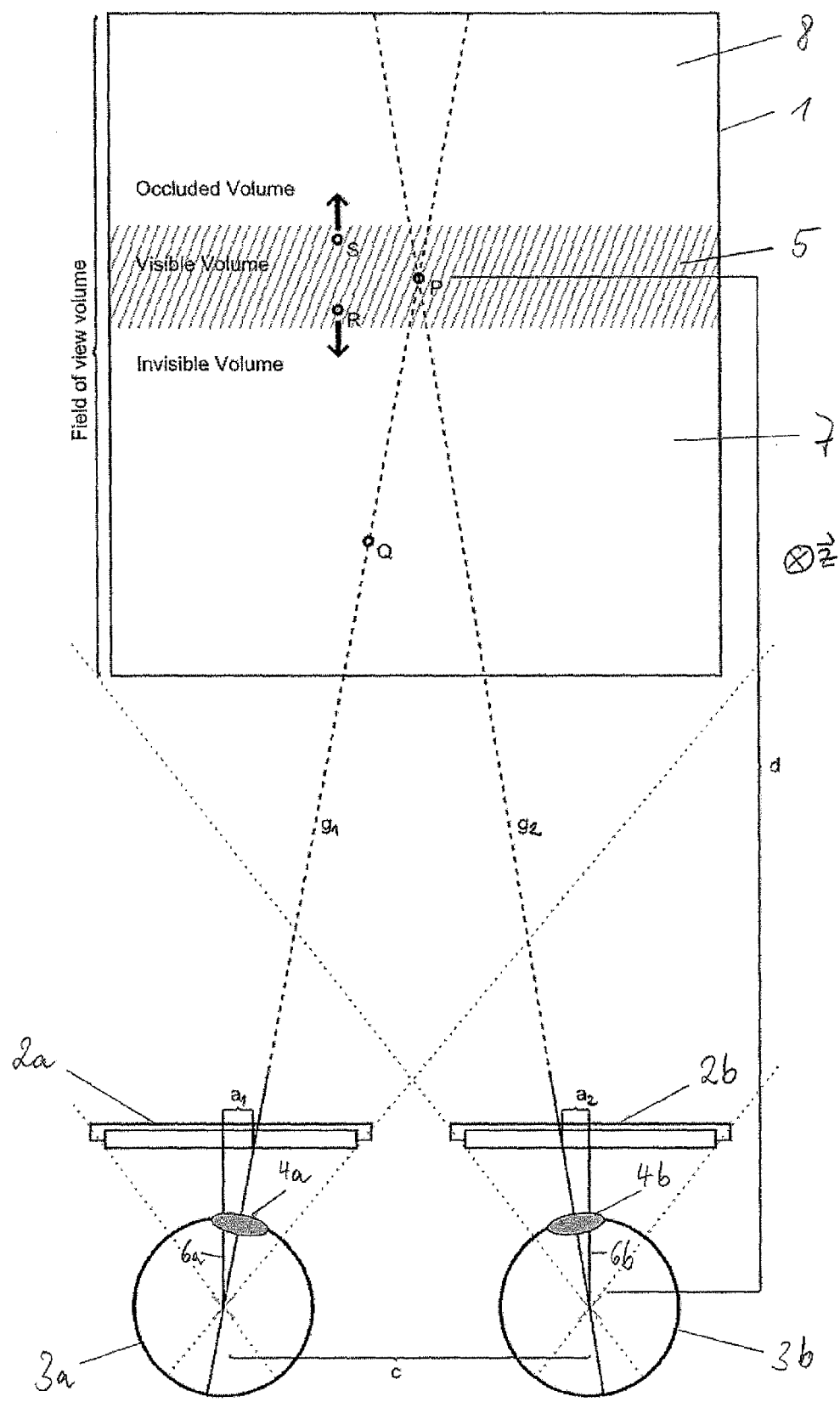
FIG. 2a shows a first embodiment for determining a visible volume with moving graphical navigation features.

FIG. 2a shows a visible volume 5 embodying a subset of the medical image information which is embodied by the field of view volume 1. The visible volume 5 is defined as an image volume in a predetermined neighbourhood in the drawing plane around the point of gaze P. The image units contained in the visible volume are assigned a visibility value which is indicated by the shading in FIG. 2a and designates at least partial opacity. The image features described by the image information in the visible volume are thus visible to the user. The occluded volume 8 consists of medical image information which is only partially visible (and preferably not visible, depending on the degree of opacity of the image units in the visible volume) to the user since, from the user's point of view, it lies behind the visible volume. The invisible volume 7 represents medical image information which is not visible to the user since it is assigned a visibility value designating complete transparency. The user can therefore look through invisible volume 7 in order to get a visual impression of the image features in the visible volume.

In the visible volume 5, graphical navigation features S and R are displayed with a predetermined and preferably fixed spatial relationship relative to the point of gaze P in the common reference system. The graphical navigation features S and R preferably move in the common reference system in accordance with moving the point of gaze P. The graphical navigation features S, R in this case take the form of two small circles. If the user shifts his point of gaze away from P to for example S, the visible volume 5 will be moved further away from the position of the user, in particular further away from the position of his eyes 3a, 3b in the common reference system. The user is then able to get a visual impression of image features described by medical image information having positions in the common reference system which lie in the occluded volume 8. If in turn the user shifts his point of gaze to R, the visible volume 5 will move towards the user, in particular towards the positions of his eyes 3a, 3b, in the common reference system (i.e. from the user's point of view). This allows the user to get a visual impression of the image features having positions which lie in the invisible volume 7. According to a preferred embodiment, when the user shifts the position of the visible volume 5 in the drawing plane, a visibility value designating complete opacity is assigned to the image units lying at the positions in the common reference system to which the visible volume 5 is shifted. The user is therefore offered the possibility to navigate through the field of view volume 1 in the drawing plane and change his depth of sight into the field of view volume 1.

Figure 2B:
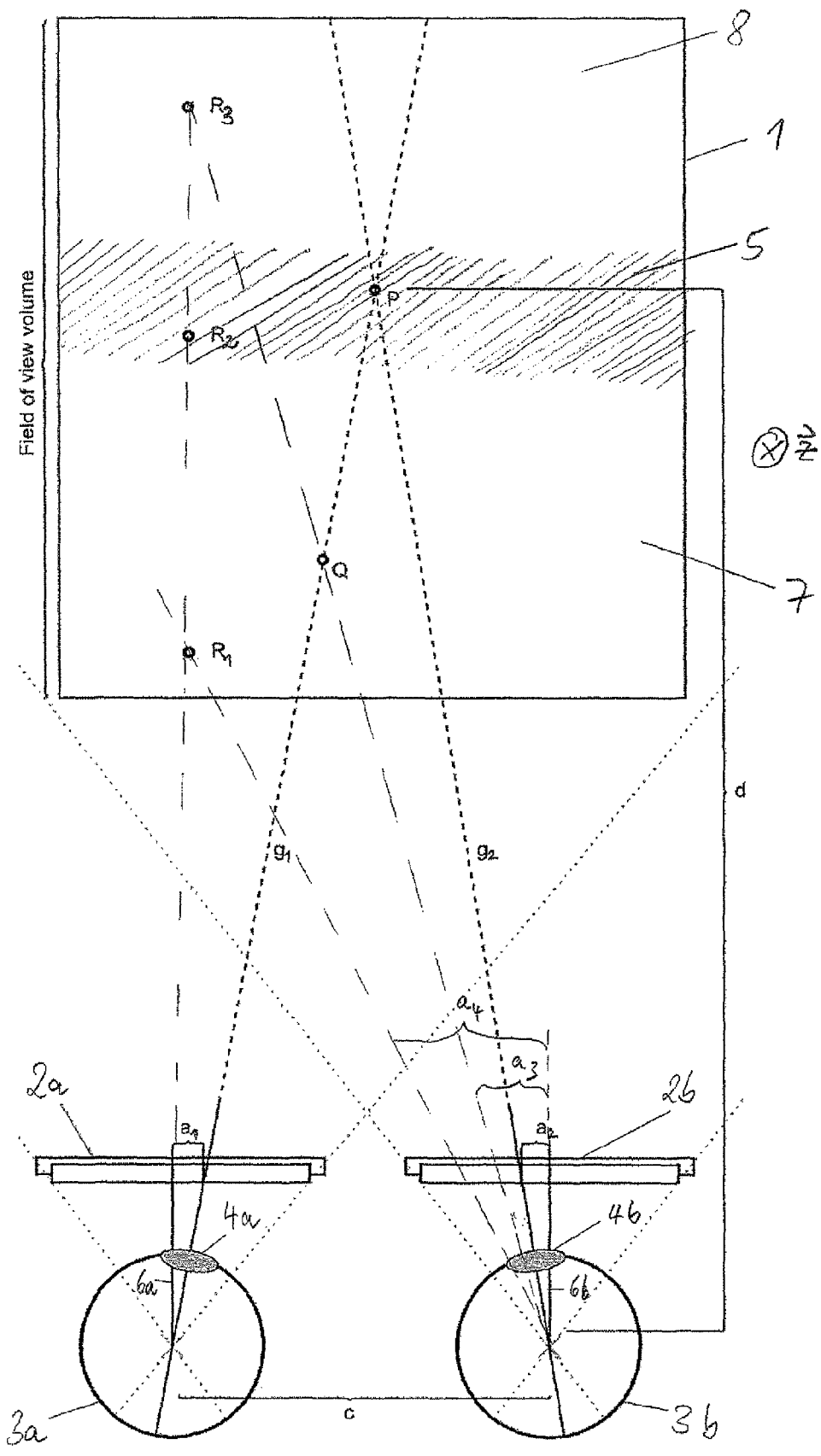
FIG. 2b shows a first embodiment of determining a visible volume with fixed graphical navigation features.

The embodiment of FIG. 2b basically corresponds to the embodiment of FIG. 2a with the exception of graphical navigation features $R_1$, $R_2$ and $R_3$ being displayed at fixed positions in the common reference system as an overlay to the visible volume 5 irrespective of the position of the point of gaze P. In particular, the graphical navigation features $R_1$, $R_2$, $R_3$ rest in the common reference system. In this case, also a graphical navigation feature $R_3$ lying in the occluded volume 8 is visible to the user. If the user looks at one of the graphical navigation features $R_1$, $R_2$ or $R_3$, the visible volume 5 will be shifted to a neighbourhood lying around the graphical navigation feature $R_1$, $R_2$ or $R_3$ at which the user is gazing. He will then be able to view the medical image information lying in that neighbourhood. In the case of FIG. 2b, the user has looked at graphical navigation feature $R_2$ such that he is able to gaze at all positions in the common reference system lying in the shaded neighbourhood around the position of $R_2$ without moving the visible volume 5. In particular, he can get a visual impression of all image features lying in the respective neighbourhood around $R_2$. In the case of FIG. 2b, the positions of $R_1$, $R_2$ or $R_3$ are displayed correctly a line i.e. along one straight line in the drawing plane which runs perpendicular to the screens 2a, 2b. In the present case, the user is offered a three-dimensional display of $R_1$ and $R_3$ and gazing at one of the moved visible volumes to the predetermined neighbourhood around $R_1$ or $R_3$, respectively. The user is thus able to navigate, i.e. move the visible volume 5, through the field of view volume 1 along the discrete positions of $R_1$, $R_2$ or $R_3$.

It is notable that $R_1$, $R_2$ or $R_3$ will have different distances from the neutral lines of view 6a, 6b on the screens 2a and 2b, respectively, since they do not lie in a central viewing plane which runs perpendicular to the drawing plane and parallel to the neutral lines of view 6a, 6b. This has the effect that the user is offered a spatial impression of in the case of FIG. 2b $R_1$ and $R_3$ and thus is able to tell which one of $R_1$ and $R_3$ has a position in the common reference system which is closer to or further away, respectively, from his point of view. In the case of FIG. 2b, the left-eye visual impression is that $R_1$ and $R_3$ lie on the neutral line of sight 6a, whereas the right-eye visual impression is that $R_1$ lies a distance $a_4$ away from the right-eye neutral line of sight 6b on the screen 2b and $R_3$ lies a distance $a_3$ away from the right-eye neutral line of sight 6b on the screen 2b, wherein $a_4>a_3$. By including the visual information from his right eye 3b, the user is thus able to tell, from the generally two-dimensional display on the screens 2a, 2b that from his point of view, $R_1$ is closer to him than $R_3$. He can therefore decide which one of $R_1$ and $R_3$ to use to move the visible volume 5 in the desired direction.

The invention claimed is:

1. A viewing system for viewing medical image information, comprising:
a computer having a processor configured to process medical image data for determining a set of displayed medical image data to be displayed, the computer executing, on the processor, steps of:
a) acquiring, at the processor, the medical image data comprising three-dimensional medical image information describing an anatomical structure, and displaying the medical image information with a visibility value describing the opacity and/or transparency of the medical image information;
b) acquiring, at the processor, navigation display feature data comprising navigation display feature information describing at least one graphical navigation feature;
c) displaying, based on data determined by the processor, the navigation display feature information simultaneously with the medical image information;
d) acquiring, at the processor, viewing direction data from a tracking unit, the viewing direction data comprising viewing direction information describing a spatial relationship of a viewing direction of a user relative to the position of the at least one graphical navigation feature which is displayed in the same image as the medical image information;
e) determining, by the processor and based on the viewing direction data, image information subset data comprising image data subset information describing a subset of the medical image information to be selected for display, wherein the subset of the medical image information describes a part of the anatomical structure but not the whole anatomical structure, and wherein the subset of the medical image information represents a visible image of a first part of the anatomical structure which lies in between a different, second part of the anatomical structure which is displayed in a transparent manner and a further different, third part of the anatomical structure which is occluded in the display;
a display device for displaying the medical image information and the navigation display feature information; and
the tracking unit tracking the eyes of the user and preferably the orientation of the user's head.

2. A computer-implemented medical image processing method for determining a set of medical image data to be displayed, the method comprising
executing, on a processor of a computer, the steps of:
a) acquiring, at the processor, medical image data comprising three-dimensional medical image information describing an anatomical structure, and displaying the three-dimensional medical image information with a visibility value describing the opacity and/or transparency of the three-dimensional medical image information;
b) acquiring, at the processor, navigation display feature data comprising navigation display feature information describing at least one graphical navigation feature;
c) displaying, based on data determined by the processor, the navigation display feature information simultaneously with the three-dimensional medical image information;
d) acquiring, at the processor, viewing direction data comprising viewing direction information describing a spatial relationship of a viewing direction of a user relative to a position of the at least one graphical navigation feature which is displayed in the same image as the medical image information;
e) determining, by the processor and based on the viewing direction data, image information subset data comprising image data subset information describing a subset of the medical image information to be selected for display, wherein the subset of the medical image information describes a part of the anatomical structure but not the whole anatomical structure, and wherein the subset of the medical image information represents a visible image of a first part of the anatomical structure which lies in between a different, second part of the anatomical structure which is displayed in a transparent manner and a further different, third part of the anatomical structure which is occluded in the display.

3. The method according to claim 2, wherein the viewing direction information and the navigation display feature information are defined in or transformed into a reference system used to display the medical image information.

4. The method according to claim 2, wherein the graphical navigation feature is displayed as an overlay on the medical image information.

5. The method according to claim 2, wherein the viewing direction information comprises point of gaze information about the position of a point of gaze of the user.

6. The method according to claim 5, wherein the point of gaze is determined based on tracking the eyes of the user with a tracking unit and determining an intersection of the viewing direction with a display plane of a display device used for displaying the medical image information.

7. The method according to claim 6, wherein the subset of the medical image information represents an image volume around a point of interest, the position of the point of interest being determined according to the position of the point of gaze.

8. The method according to claim 2, wherein the medical image information contained in the subset of the medical image information is assigned a visibility value lying in between a value describing complete opacity and a value describing complete transparency, but is not assigned a visibility value describing complete opacity or complete transparency.

9. The method according to claim 7, wherein the medical image information representing the second part of the anatomical structure is assigned a visibility value representing complete transparency and wherein the display of the first part of the anatomical structure and the display of the third part of the anatomical structure are divided by medical image information having a visibility value representing complete opacity.

10. The method according to claim 9, wherein the size of the second part of the anatomical structure, in particular the number of image units in the medical image information representing the second part, is determined, in particular increased or decreased, based on the point of gaze.

11. The method according to claim 10, wherein the viewing direction information describes the orientation of the user's head in a reference system in which the positions of the medical image information is described, and wherein the image information subset data is determined based on the information about the orientation of the user's head.

12. A non-transitory computer-readable program storage medium storing program which, when running on a processor of a computer or when loaded into a memory of the computer, causes the processor to perform a computer-implemented medical image processing method for determining a set of medical image data to be displayed, the method comprising executing, on the processor, steps of:
 a) acquiring, at the processor, medical image data comprising three-dimensional medical image information describing an anatomical structure, and displaying the medical image information with a visibility value describing the opacity and/or transparency of the image information;
 b) acquiring, at the processor, navigation display feature data comprising navigation display feature information describing at least one graphical navigation feature;
 c) displaying, based on data determined by the processor, the navigation display information simultaneously with the medical image information;
 d) acquiring, at the processor, viewing direction data comprising viewing direction information describing a spatial relationship of a viewing direction of a user relative to the position of the at least one graphical navigation feature which is displayed in the same image as the medical image information;
 e) determining, by the processor and based on the viewing direction data, image information subset data comprising image data subset information describing a subset of the medical image information to be selected for display, wherein the subset of the medical image information describes a part of the anatomical structure but not the whole anatomical structure, and wherein the subset of the medical image information represents a visible image of a first part of the anatomical structure which lies in between a different, second part of the anatomical structure which is displayed in a transparent manner and a further different, third part of the anatomical structure which is occluded in the display.

13. A computer, comprising the program storage medium of claim 12.

* * * * *